United States Patent [19]

Nedungadi et al.

[11] Patent Number: 5,722,997
[45] Date of Patent: Mar. 3, 1998

[54] METHOD AND APPARATUS FOR CARDIAC IMPEDANCE SENSING

[75] Inventors: Ashok P. Nedungadi, Lake Oswego, Oreg.; Behrad Aria, Sugar Land, Tex.

[73] Assignee: Sulzer Intermedics Inc., Angleton, Tex.

[21] Appl. No.: 714,881

[22] Filed: Sep. 17, 1996

[51] Int. Cl.⁶ ........................................ A61N 1/37
[52] U.S. Cl. ............................. 607/28; 128/734
[58] Field of Search .................. 607/8, 6, 4, 5, 607/27, 28; 128/734, 693

[56] References Cited

U.S. PATENT DOCUMENTS

| | | | |
|---|---|---|---|
| 4,140,132 | 2/1979 | Dahl | 128/419 |
| 4,291,699 | 9/1981 | Geddes | 178/419 |
| 4,688,573 | 8/1987 | Alt | 128/419 |
| 4,702,253 | 10/1987 | Nappholz | 128/419 |
| 4,899,750 | 2/1990 | Ekwall | 607/28 |
| 5,003,975 | 4/1991 | Hafelfinger et al. | 607/28 |
| 5,115,807 | 5/1992 | Pless et al. | 607/8 |
| 5,137,019 | 8/1992 | Pederson et al. | 128/419 |
| 5,174,286 | 12/1992 | Chirife | 128/419 |
| 5,197,467 | 3/1993 | Steinhaus | 128/419 |
| 5,201,808 | 4/1993 | Steinhaus | 128/419 |
| 5,201,865 | 4/1993 | Kuehn | 607/28 |
| 5,391,190 | 2/1995 | Pederson et al. | 607/23 |
| 5,431,692 | 7/1995 | Hansen et al. | 607/28 |
| 5,507,785 | 4/1996 | Deno | 607/24 |
| 5,578,064 | 11/1996 | Prutchi | 128/901 |
| 5,607,455 | 3/1997 | Armstrong | 607/8 |

Primary Examiner—William F. Kamm
Assistant Examiner—Kennedy J. Schaetzle
Attorney, Agent, or Firm—John R. Merkling

[57] ABSTRACT

A method and apparatus for measuring impedance of heart tissue or the leads associated with a cardiac stimulation apparatus involves charging a capacitor, storing the value of the voltage across the capacitor when charged, discharging the capacitor into said lead/heart system and storing the voltage on said capacitor when discharged. The two voltages may then be used to determine the combined impedance of the lead and the heart tissue. This may be advantageously accomplished by using separate circuits to measure each of the voltages of the capacitor and storing those voltages. These voltages then may be applied to an analog-to-digital converter which converts the ratio of said voltages to digital form. This value can then be used to calculate the combined impedance of the heart tissue or the lead. If one of the two impedances is known the other can then be easily determined.

18 Claims, 2 Drawing Sheets

METHOD AND APPARATUS FOR CARDIAC IMPEDANCE SENSING

TECHNICAL FIELD

Our invention relates to the field of cardiac impedance sensing and more particularly to a technique for low power impedance sensing.

BACKGROUND OF OUR INVENTION

Implanted cardiac pacemakers are employed to assist patients suffering from severe bradycardia or chronotropic incompetence. Originally, such pacemakers restored a normal, at rest, heart rate by providing either a fixed rate or a narrow range of externally programmable rates. However, these pacemakers failed to meet patients' metabolic demands during exercise. Consequently, so-called "rate adaptive" or "rate responsive" pacemakers were developed. These pacemakers sense some parameter correlated to physiologic need and adjust the pacing rate of the pacemaker accordingly.

Numerous parameters have been selected to attempt to correlate pacing rate to the actual physiologic need of the patient. Blood pH, blood temperature, QT interval, vibration, respiration rate, or accelerations due to physical activity have been employed with varying degrees of success. Also, the stroke volume of the heart and the minute volume of respiration may be inferred from impedance measurements. The stroke volume of the heart is defined as the volume of blood expelled by the ventricle in a single beat. It is equal to the difference between the end diastolic volume and the end systolic volume. In normal human subjects with healthy hearts, the stroke volume of the heart has been found to remain relatively constant over a wide range of exertion. Increases in cardiac output required to meet physiologic needs are primarily provided by increased heart rate. The heart may attempt to increase its stroke volume during exertion. The stroke volume cannot increase, however, by a factor of more than about two or two and half times. Increasing the pacing rate is therefore still desired. One may utilize the body's tendency to attempt to increase stroke volume to adjust the pacing rate of an implanted pacemaker, thereby providing an appropriate physiologic pacing rate.

Various pulse-based impedance sensors have been proposed or are now in use with cardiac stimulators for deriving hemodynamic and other physiologic parameters. These sensors deliver trains of fairly low-energy probing pulses between two or more electrodes of a pacing or defibrillation lead system. Each train contains pulses delivered at the rate of 1 to 500 per second. In general, these pulses have a biphasic morphology in order to balance the charge delivered to tissue, thus avoiding ion migration and electrolysis within the living tissue, as well as reducing interference on external monitoring equipment. In addition, charge balancing reduces the possibility of actually capturing the heart muscle with low-threshold leads.

The impedance sensor may be implemented as described by Salo et al. in U.S. Pat. No. 5,190,035 by injecting a relatively low frequency carrier signal (under 5 KHz) between spaced electrodes disposed within the body. The beating action of the heart and movement of the chest (because of respiration) modulate this carrier due to changes in sensed impedance between electrodes implanted within the body. Similar approaches have been described in a number of patents, for example by Geddes in U.S. Pat. No. 4,291,699 and Pederson et al. in U.S. Pat. Nos. 5,137,019 and 5,391,190.

U.S. Pat. No. 5,197,467 to Steinhaus, et al. describes charging a capacitor (see particularly FIG. 2) and discharging the capacitor through the heart or a portion of the body for a selected brief interval. The voltage remaining on the capacitor after the period of discharge can be detected through a buffer, converted to digital information, and used to estimate the impedance of that portion of the patient's body between the cathode and anode electrodes.

Impedance measurements are valuable not only in diagnostic applications, but they may also be useful for detecting intermittent or permanent lead failure. While existing impedance measuring systems may be capable of determining whether there is lead failure, they may be too expensive and too costly in terms of battery power consumption to be feasible for detecting lead failure.

While existing systems are highly advantageous, it would be desirable to have an impedance measuring system which is amenable to very low power implementations. It would also be desirable to have an impedance measuring system that could be implemented at low cost.

SUMMARY OF OUR INVENTION

In accordance with one embodiment of our invention, a cardiac stimulation apparatus includes a stimulator arranged to stimulate the patient's heart. An impedance measuring circuit has a charging circuit and a capacitor. The charging circuit is arranged to charge the capacitor and the capacitor is adapted to produce a pulse when the capacitor is discharged. A means is provided for electrically transmitting the pulse through at least a portion of the patient's body. A circuit develops signals representative of the voltages across the capacitor when charged and when said capacitor has been discharged to produce the pulse.

In accordance with still other embodiments of the present invention an analog-to-digital converter useful in connection with the cardiac stimulation apparatus includes two inputs. A reference input to the analog-to-digital converter receives a voltage signal when the capacitor has been charged. The other input to the analog-to-digital converter receives a voltage signal when the capacitor has been discharged such that the analog-to-digital converter produces a signal representative of the ratio of the discharged to the undischarged voltages across the capacitor.

A method for cardiac stimulation includes the step of charging a capacitor to a first voltage. The first voltage is stored when the capacitor is charged. The capacitor is then discharged into heart tissue. The voltage across the capacitor when the capacitor has been discharged is also stored.

DETAILED DESCRIPTION OF OUR PREFERRED EMBODIMENT

Figure 1:
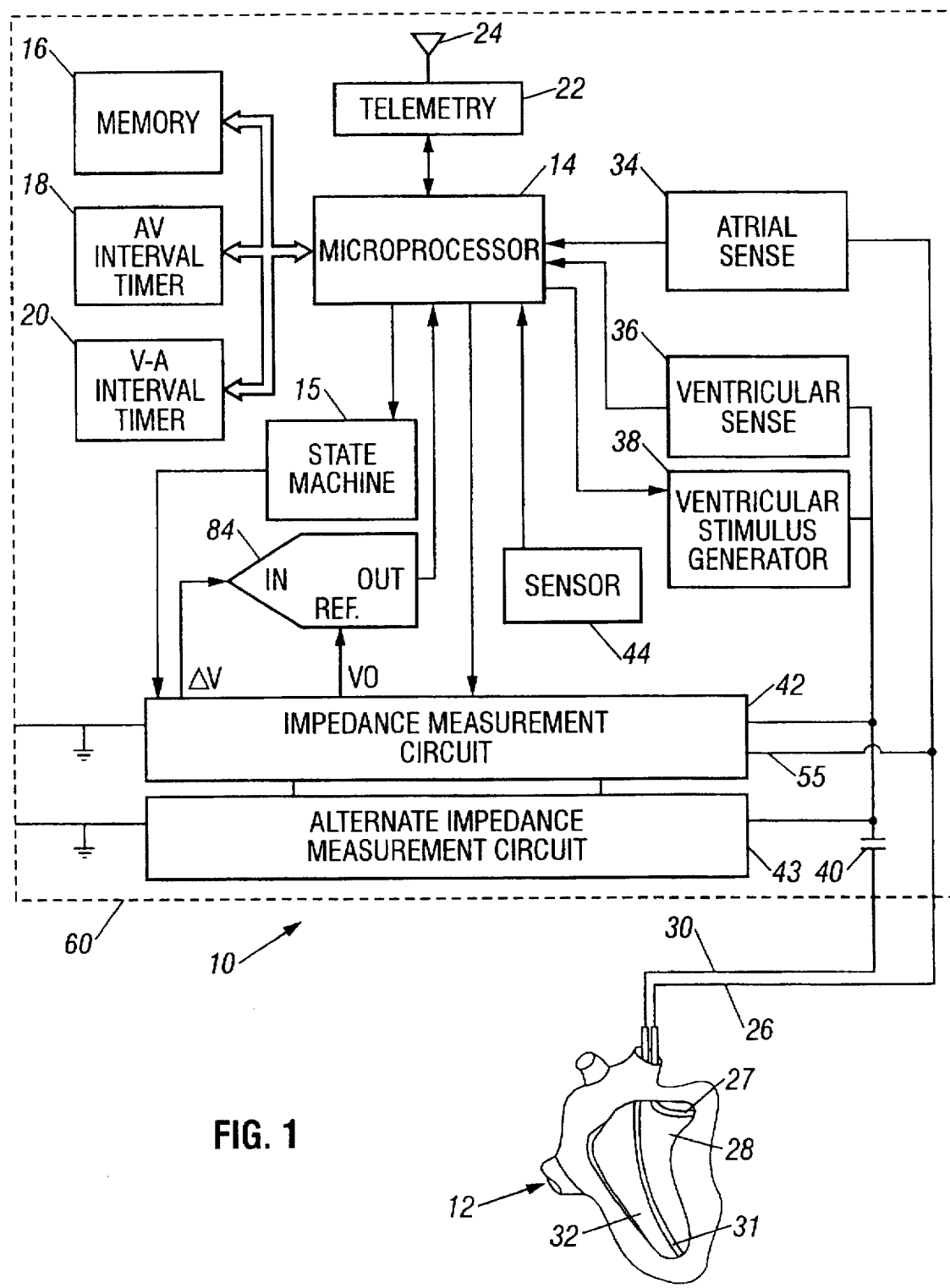
FIG. 1 is a block diagram of a rate adaptive pacemaker according to an embodiment of our invention.

We will now describe the preferred embodiment of our invention with reference to the accompanying figures. Like numerals will be used to designate like parts throughout. Referring now to FIG. 1, a pacemaker, generally designated 10, is illustrated in schematic fashion with connection to a human heart 12. For ease of illustration, we have elected to describe our invention in connection with a pacemaker having atrial sensing and ventricular sensing and pacing. It should be understood, however, that our invention can be employed in connection with an apparatus for sensing in the atrium, the ventricle or both and that both atrial or ventricular pacing or either of them could be provided without departing from the teachings of our invention. Our invention could also be implemented in an apparatus that includes an implantable defibrillator/cardioverter.

With this understanding, the illustrated pacemaker 10 comprises a microprocessor 14 which executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 may be provided. Similarly, a V-A interval timer 20 may also be provided, as known in the art. The microprocessor is provided with a telemetry circuit 22 to enable communication, across an antenna 24, with an external programmer (not shown). Telemetry permits an attending physician to obtain data and information from the pacemaker and to set various selectable pacemaker control parameters, as known in the art.

The pacemaker 10 is connected to the heart 12 through a first lead 26 to an electrode 27 in the atrium 28 and through a second lead 30 to an electrode 31 in the ventricle 32. An indifferent electrode (e.g., the pacemaker can) is provided to complete the electrical circuit through the body. In the illustrated embodiment, a can or outer casing 60 of the pacemaker serves as the indifferent electrode. Bipolar leads can also be used with our invention as well as the unipolar leads illustrated here. Atrial electrogram sensing, through an atrial sense circuit 34, and ventricular sensing, through a ventricular sense circuit 36, provide information to the microprocessor concerning the condition and responsiveness of the heart. In addition, pacing pulses are provided to the ventricle from a ventricular stimulus generator 38. It is clearly within the scope of those skilled in the art to provide cardioversion/defibrillation capabilities in response to the detected condition of the heart. Stimulation to the heart is passed through a coupling capacitor 40.

To control the pulse rate of the ventricular stimulus generator 38, the microprocessor 14 acquires information on the condition of the heart through an impedance circuit 42. The impedance circuit 42 detects changes in impedance, for example, due to the changing shape of the heart as it beats and pumps blood. This information can be used to derive a measure of the stroke volume or ejection fraction or end diastolic volume of the heart. Furthermore, the shape of the impedance waveform can provide information on other cardiac timing parameters such as isovolumetric contraction time or pre-ejection period. A backup or alternate impedance measuring circuit 43 may also be provided.

Sensor 44 may also be provided to obtain an indication of physiologic need and to adjust the pacing rate. Such a sensor may be an accelerometer, as described by Dahl, U.S. Pat. No. 4,140,132 (incorporated herein by reference), a temperature sensor, as described by Alt, U.S. Pat. No. 4,688,573 (also incorporated herein by reference), or any other suitable sensor of a parameter which may be correlated to physiologic need of the patient.

Figure 2:
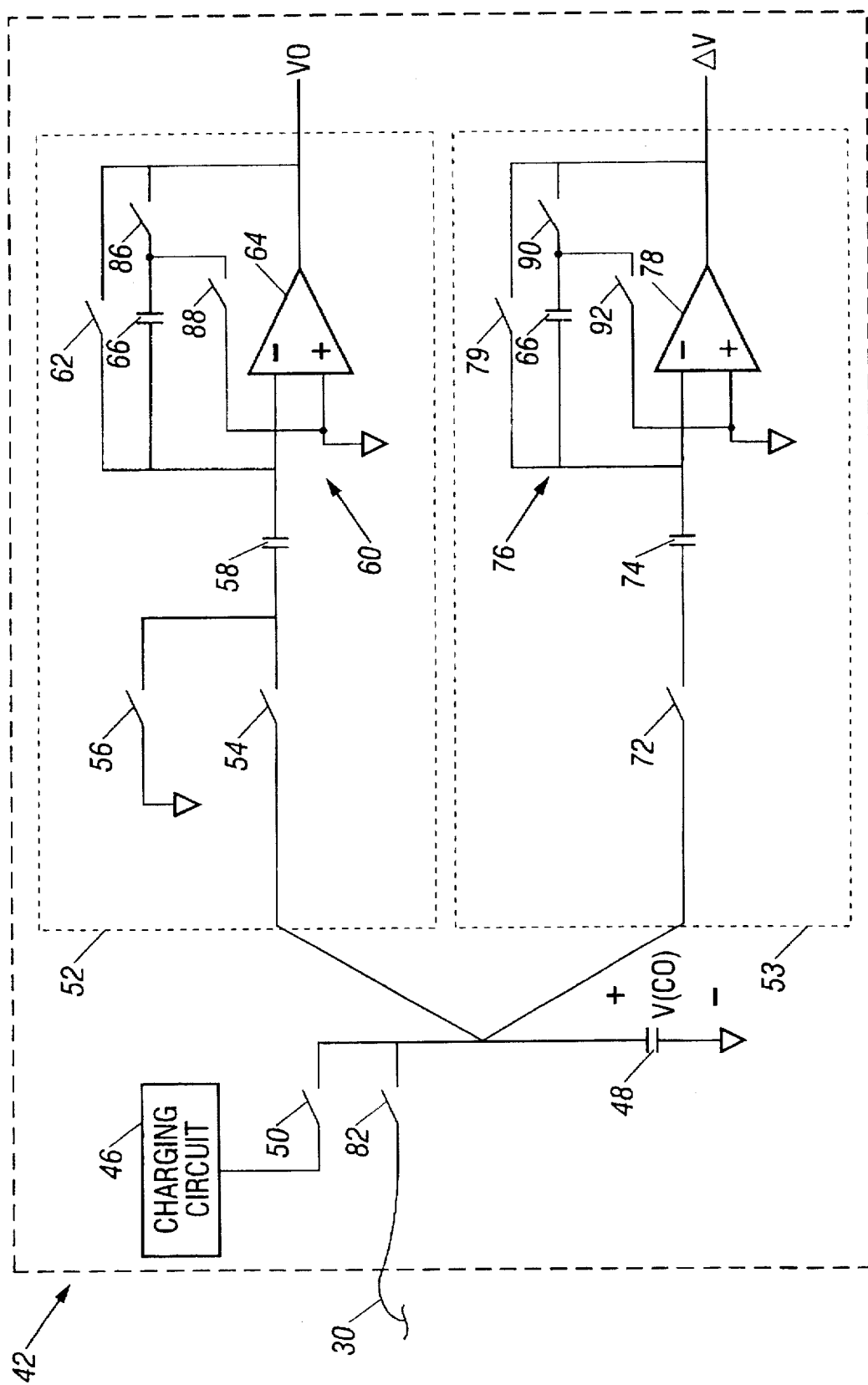
FIG. 2 is a circuit diagram showing an impedance measuring circuit in accordance with our invention.

Impedance circuit 42, shown in FIG. 2, includes circuitry for measuring ventricular impedances. An identical circuit (not shown) could also be provided to the atrium 28 chamber and lead 26, using the connection 55 or a switching system (not shown) could be used to create pulses for the atrium 28 and lead 26. The circuit 42 comprises a charging circuit 46 and a capacitor 48 connected through a switch 50 so as to be charged by said charging circuit 46 when the switch 50 is closed. The capacitor 48 is also connectable to first and second signal detectors 52 and 53. The first signal detector 52 includes switches 54 and 56, a capacitor 58, and a sample-and-hold circuit 60 with a switch 62 connected across it. The sample-and-hold circuit 60 includes an amplifier 64 and a capacitor 66 configured as an integrator. The output of the detector 52 is a signal VO which may, for example, be indicative of the charge on the capacitor 48 when fully charged.

The capacitor 48 also connects to the detector 53 which outputs a signal $\Delta V$ which is indicative of the loss of voltage across the capacitor 48 when the capacitor is discharged into the heart tissue. As a result of the impedance of the lead 30 and the heart 12, a voltage drop on the capacitor 48 occurs when the capacitor 48 produces a pulse which is transmitted through the heart tissue and the lead 30. The capacitor 48 can be connected via the switch 72 to the capacitor 74, the sample-and-hold circuit 76 and the switch 79. The sample-and-hold circuit 76 includes an amplifier 78 and a capacitor 80 connected as an integrator with the switch 79 connected across the integrator.

The circuit 42 operates generally as follows. The switches 62, 79, 50, 88 and 92 are closed, while the switches 86 and 90 are opened under control of the microprocessor 14 and state machine 15. As a result, the capacitor 48 is charged to a voltage level V(CO) determined by the charging circuit 46. VO and $\Delta V$ are set to the same voltage level present at the positive inputs to the amplifiers 64 and 78 which is circuit ground reference, and the input offset of amplifier 64 and 78 are stored across the capacitor 66 and capacitor 80 respectively. Next, switch 50 is opened. All nodal voltages remain unchanged. Then switches 54 and 72 are closed causing the capacitors 58 and 74 to be charged to the same voltage level V(CO) stored across the capacitor 48.

Next the switches 62, 54, 79, 88 and 92 are opened, and switches 86 and 90 are closed and then switch 56 is closed. Again all the nodal voltages remain unchanged except for the voltage VO and the voltage across capacitor 58. The value VO is equal to minus the initial voltage across the capacitor 48 before a pacing pulse is produced (V(CO)) times the ratio of the capacitance of the capacitor 58 over the capacitance of the capacitor 66:

$$VO = -(C_{58}/C_{66})V(CO)$$

To produce a pacing pulse, the switch 82 is closed for a controlled length of time T. As a result, the capacitor 48 discharges through the lead 30 into the heart 12. At the end of the time interval T, the switches 72 and 82 are opened causing the voltage $\Delta V$ to become the scaled, sampled-and-held value of the droop across the capacitor 48 during the pacing as a result of the impedance of the heart 12 and the lead 30. The voltage $\Delta V$ is given by the following equation:

$$\Delta V = -(C_{74}/C_{80})V(CO)(1-e^{-T/\tau})$$

where $$\tau = RL \times C_{48}$$

and RL is the total impedance presented by the lead and the heart tissue.

For known values of T and known values of capacitor 48 capacitance, and measured values of VO and ΔV, the value of RL can be calculated as:

$$RL = \frac{-T/C_{48}}{\ln[1 - \alpha(\Delta V/VO)]}$$

where:

$$\alpha = C_{66}C_{80}/C_{58}C_{74}$$

Since the measurement depends on the ratios of integrated capacitors which can be very accurate and not on their absolute values, it can be appreciated that the impedance measurement circuit 42 provides a reasonably accurate measurement of total impedance with very low expenditure of battery power.

Thus the present invention may be used in conjunction with other impedance measuring circuits. For example, the present invention can be used on an ongoing basis to measure either heart impedance or lead impedance. When an impedance problem is detected the pacemaker can switch to a more accurate impedance measuring circuit 43, such as the circuit disclosed in the U.S. Pat. No. 5,507,785 to Deno, which is hereby expressly incorporated by reference herein. The advantage of this approach would be that with the present invention, the power dissipation is extremely low. More accurate measuring techniques can be used only when necessary so that power is conserved to the greatest possible extent.

As shown in FIG. 1 the impedance measurement circuit 42 may supply data to the microprocessor 14. The opening and closing of the switches shown in FIG. 2 may be implemented under the control of the microprocessor 14 in conjunction with the state machine 15. The analog values of ΔV and VO are converted into digital values using the A-to-D converter 84. These values can then be stored in the memory 16. The microprocessor 14 and the system software will then use these values to calculate the impedance according to the equation set forth above for RL.

Using both detectors 52 and 53, the detector 52 measures and holds the voltage VO while the detector 53 measures and holds the voltage ΔV as explained previously. The signal VO is fed into the reference input of the A-to-D convertor 84, as shown in FIG. 1. The signal ΔV is fed into the signal input of the A-to-D converter 84. At the end of the conversion, the output of the A-to-D converter 84 contains the normalized value of ΔV with respect to VO, which is the ratio of ΔV/VO required to solve the equation for the value of RL, the total load impedance.

This arrangement is advantageous since it only requires one analog-to-digital conversion. In addition it imposes less overhead on the system software since it readily presents the ratio ΔV/VO, eliminating the calculation of that value by the system processor. In addition, conversion accuracy is improved due to the normalization, especially for small values of ΔV. Overall, the throughput of this method for the number of conversions possible in a given interval is particularly high.

The present invention may be used to measure lead impedance for both atrial and ventricular leads. In these applications, there can be one lead impedance measurement circuit per lead or the circuit could be shared (multiplexed) between the two leads.

In accordance with another embodiment of the present invention, the detector 53 can be eliminated. In this case the detector 52 is used to obtain the signals VO and ΔV sequentially. This method involves two A-to-D conversions. The conversions could take place in alternative pacing pulses, making impedance measurements available only on every other pulse, or if a fast A-to-D converter is available, it can be performed on each pacing pulse.

This will put the demand on the A-to-D converter and would require faster settling time for the amplifier 64. This is especially so when the detector 52 is shared between atrial and ventricular leads. In addition, some gain ranging could be required when the values of V(CO) and ΔV are very far apart, such as the situation which arises when V(CO) and RL are very large and the interval T, is short.

Another advantage of the first embodiment is that it is inherently auto-zeroing. At the beginning of each measurement cycle, the offset voltages between the two input terminals of the amplifiers 64 and 78 are sampled and stored on the capacitors 66 and 80 thereby eliminating the inaccuracies due to input offsets for the particular amplifiers utilized.

Because the present invention may be implemented with fully integratable CMOS technology, circuit topology is very simple and readily lends itself to being interfaced with the rest of the pacemaker implantable cardioverter/defibrillation system.

In addition, circuit 42 can be power strobed. In this way it consumes power only when it is in use. However, even in the operating mode, the amplifiers 64 and 78 consume very little power.

Our invention may be embodied in other specific forms without departing from the spirit or essential characteristics thereof. The foregoing description is, therefore, to be viewed in all respects as illustrative and not restrictive. The scope of our invention is defined by the appended claims.

We claim as our invention:

1. A cardiac stimulation apparatus comprising:

a stimulator arranged to stimulate a patient's heart;

a charging circuit and a first capacitor, said charging circuit arranged to charge said first capacitor and said first capacitor adapted to produce a pulse when said first capacitor is discharged;

means for electrically transmitting said pulse through at least a portion of the patient's body;

a first impedance measuring circuit for developing a first signal representative of the voltage across said first capacitor when charged and a second signal representative of the voltage across said first capacitor when said first capacitor has been discharged to produce said pulse, said first impedance measuring circuit periodically measuring the impedance, and a second impedance measuring circuit, means for detecting an impedance imbalance, and means for activating said second impedance measuring circuit when said impedance imbalance is detected.

2. The apparatus of claim 1 including a first circuit for developing said first signal representative of the voltage across said first capacitor when charged and a second circuit for developing said second signal representative of the voltage across said first capacitor when said capacitor first has been discharged.

3. The apparatus of claim 2 including sample-and-hold circuits for storing the signals representative of said voltages across said first capacitor.

4. The apparatus of claim 1, including an analog-to-digital converter having a reference input and a signal input, the reference input to said analog-to-digital converter connected to receive said first signal and said signal input to said analog-to-digital converter connected to receive said second signal for producing a signal representative of a ratio of the discharged voltage to the charged voltage across said first capacitor.

5. The apparatus of claim 1 further comprising a first detector circuit connected to said first capacitor, said first detector circuit having a first switch, a second capacitor, and a first sample-and-hold circuit, wherein said first capacitor is connected via said first switch to said second capacitor and said second capacitor is connected to said first sample-and-hold circuit for producing an output signal representative of the voltage on the first capacitor when charged.

6. The apparatus of claim 5 wherein said first sample-and-hold circuit comprises an integrated circuit amplifier having two input terminals and wherein said apparatus further comprises a second capacitor arranged to store the offset voltage between the two input terminals to the integrated circuit amplifier of said first sample-and-hold circuit, thereby eliminating inaccuracies due to input offsets.

7. The apparatus of claim 5 including a second detector circuit connected to said first capacitor, said second detector circuit including a second switch connected to said first capacitor, and a third capacitor connected to said second switch and a second sample-and-hold circuit connected to said fourth capacitor, said second detector circuit producing an output signal indicative of the voltage on said first capacitor after a pulse is provided to the heart.

8. The apparatus of claim 7 wherein said second sample-and-hold circuit comprises an integrated circuit amplifier having two input terminals and wherein said apparatus further comprises a fifth capacitor is arranged to store the offset voltage between the two input terminals to the integrated circuit amplifier of said second sample-and-hold circuit, thereby eliminating inaccuracies due to input offsets.

9. The apparatus of claim 1 including at least one lead for connecting said stimulator to a patient's heart and an impedance measuring circuit for each lead of said cardiac stimulation apparatus.

10. A method for cardiac stimulation comprising the steps of:
  charging a capacitor to a first voltage;
  measuring said first voltage when said capacitor is charged using a first measurement circuit to produce a first signal representative of said first voltage;
  discharging said first capacitor into heart tissue; and
  measuring the voltage on said capacitor when said capacitor has been discharged using a second measurement circuit to produce a second signal representative of said second voltage
  transforming said first and second signals into a ratio of the voltages on said capacitor when charged and when discharged,
  and converting said ratio into digital form from analog form.

11. The method of claim 10 wherein the step of transforming said first and second signals comprises applying said first signal when said capacitor is charged to a reference voltage input of an analog-to-digital converter and applying the second signal when said capacitor is discharged to an input terminal of said analog-to-digital converter.

12. A cardiac stimulation apparatus comprising:
  a stimulator arranged to stimulate a patient's heart;
  a charging circuit and a first capacitor, said charging circuit arranged to charge said first capacitor and said first capacitor adapted to produce a pulse when said first capacitor is discharged;
  means for electrically transmitting said pulse through at least a portion of the patient's body; and
  a circuit for developing a first signal representative of the voltage across said first capacitor when charged and a second signal representative of the voltage across said first capacitor when said first capacitor has been discharged to produce said pulse,
  an analog-to-digital converter having a reference input and a signal input, the reference input to said analog-to-digital converter connected to receive said first signal and said signal input to said analog-to-digital converter connected to receive said second signal for producing a signal representative of a ratio of the discharged voltage to the charged voltage across said first capacitor.

13. A cardiac stimulation apparatus comprising:
  a stimulator arranged to stimulate a patient's heart;
  a charging circuit and a first capacitor, said charging circuit arranged to charge said first capacitor and said first capacitor adapted to produce a pulse when said first capacitor is discharged;
  means for electrically transmitting said pulse through at least a portion of the patient's body; and
  a circuit for developing a first signal representative of the voltage across said first capacitor when charged and a second signal representative of the voltage across said first capacitor when said first capacitor has been discharged to produce said pulse, said signal developing circuit comprising a first detector circuit connected to said first capacitor, said first detector circuit having
  a first switch,
  a second capacitor, and
  a first sample-and-hold circuit, wherein said first capacitor is connected via said first switch to said second capacitor and said second capacitor is connected to said first sample-and-hold circuit for producing an output signal representative of the voltage on the first capacitor when charged.

14. The apparatus of claim 13 wherein said first sample-and-hold circuit comprises an integrated circuit amplifier having two input terminals and wherein said apparatus further comprises a second capacitor arranged to store the offset voltage between the two input terminals to the integrated circuit amplifier of said first sample-and-hold circuit, thereby eliminating inaccuracies due to input offsets.

15. The apparatus of claim 13 including a second detector circuit connected to said first capacitor, said second detector circuit including a second switch connected to said first capacitor, and a third capacitor connected to said second switch and a second sample-and-hold circuit connected to said fourth capacitor, said second detector circuit producing an output signal indicative of the voltage on said first capacitor after a pulse is provided to the heart.

16. The apparatus of claim 15 wherein said second sample-and-hold circuit comprises an integrated circuit amplifier having two input terminals and wherein said apparatus further comprises a fifth capacitor is arranged to store the offset voltage between the two input terminals to the integrated circuit amplifier of said second sample-and-hold circuit, thereby eliminating inaccuracies due to input offsets.

17. The apparatus of claim 13 including at least one lead for connecting said stimulator to a patient's heart and an impedance measuring circuit for each lead of said cardiac stimulation apparatus.

18. A cardiac stimulation apparatus comprising:

a stimulator arranged to stimulate a patient's heart;

a charging circuit and a first capacitor, said charging circuit arranged to charge said first capacitor and said first capacitor adapted to produce a pulse when said first capacitor is discharged;

means for electrically transmitting said pulse through at least a portion of the patient's body;

a first impedance measuring circuit for periodically measuring the impedance through said portion of said patient's body, and a second impedance measuring circuit, means for detecting an impedance imbalance, and means for activating said second impedance measuring circuit when said impedance imbalance is detected.

* * * * *